US00PP17444P3

(12) United States Plant Patent
Eubanks

(10) Patent No.: US PP17,444 P3
(45) Date of Patent: Feb. 27, 2007

(54) CORN PLANT NAMED 'VENUS EXPRESS'

(50) Latin Name: *Zea diploperennis×Tripsacum laxum*
Varietal Denomination: Venus Express

(76) Inventor: Mary W. Eubanks, 8 Pilton Pl., Durham, NC (US) 27705

( * ) Notice: Subject to any disclaimer, the term of this patent is extended or adjusted under 35 U.S.C. 154(b) by 35 days.

(21) Appl. No.: 11/079,769

(22) Filed: Mar. 14, 2005

(65) Prior Publication Data

US 2006/0206973 P1 Sep. 14, 2006

(51) Int. Cl.
*A01H 5/00* (2006.01)

(52) U.S. Cl. ..... Plt./258
(58) Field of Classification Search ..... Plt./258, Plt./386
See application file for complete search history.

(56) References Cited

U.S. PATENT DOCUMENTS

PP9,640 P * 9/1996 Eubanks ..... Plt./386
5,750,828 A * 5/1998 Eubanks ..... 800/265

OTHER PUBLICATIONS

UPOV–ROM GTITM, Plant Variety Database, 2005/05, GTI Jouve Retrieval Software, Citation for Zea 'Morning Star' 2 pages.*

* cited by examiner

*Primary Examiner*—Anne Marie Grunberg
*Assistant Examiner*—June Hwu

(57) ABSTRACT

A new and distinct corn plant, which is the product of a cross between gamagrass, *Tripsacum laxum,* and diploid perennial teosinte, *Zea diploperennis.* This plant is fertile, has proven to be cross compatible with *Zea mays* L. and offers an avenue to expand the gene pool for commercial corn varieties. The instant plant is perennial with well developed rhizomes, aerenchyma tissue in its roots, abundant seed and prolific vegetation production, traits that give it improved value as a forage crop.

9 Drawing Sheets

Figure 1:
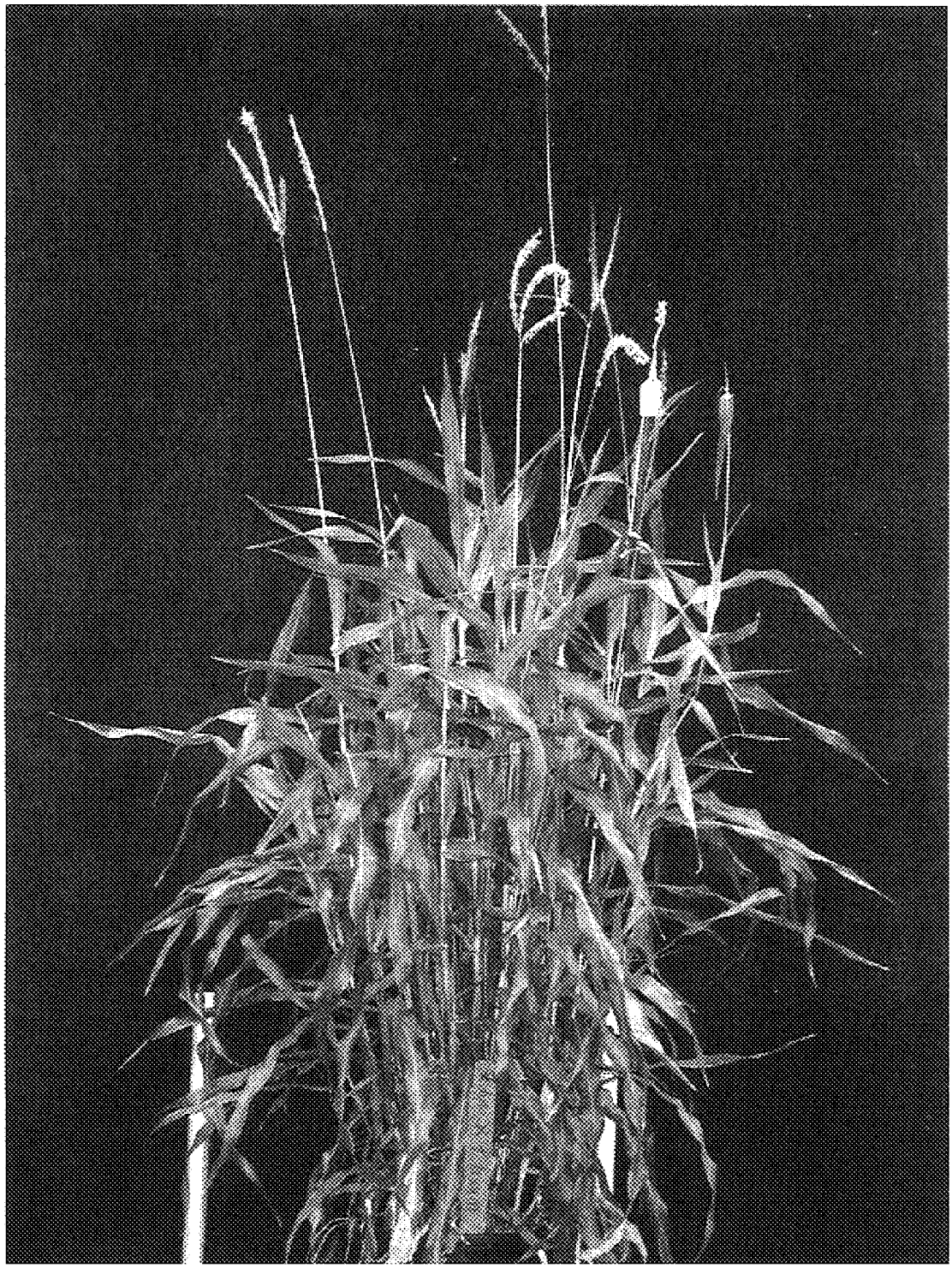

Botanical classification: *Zea diploperennis×Tripsacum laxum.*
Cultivar name: 'Venus Express'.

BACKGROUND OF THE NEW PLANT

Two wild grasses, diploid perennial teosinte, *Zea diploperennis* Iltis, Doebley and Guzman, and gamagrass, *Tripsacum laxum* Nash, have been crossed to produce a fully fertile bridge species that may improve corn, *Zea mays* L., by conferring beneficial traits such as pest resistance and drought tolerance. *Z. diploperennis* (hereinafter referred to as diploperennis), was an unknown wild relative of corn until it was discovered, apparently on the threshold of extinction, in the mountains of Jalisco, Mexico in the late 1970's. It is in the same genus as corn, has the same chromosome number as corn (n=10), and hybridizes easily with it. Gamagrass is a more distant relative of corn with a different gametic chromosome number (n=18), and varying ploidy levels ranging from 2n=36 to 2n=108. Other species of gamagrass, namely *T.dactyloides* and *T. floridanum,* have been crossed with corn and hybrids are male sterile and essentially female sterile. Attempts to cross *Tripsacum* and annual teosinte, the closest relative of corn that most scientists believe is its wild progenitor, failed. Many plant breeders believe that gamagrass has significant potential for improving corn by expanding its genetic diversity.

In 1985, crosses were made by pollinating diploperennis with pollen from Eastern gamagrass, *T. dactyloides,* U.S. Plant Pat. No. 6,906 for 'Sun Dance', the hybrid from that cross, was issued Jul. 4, 1989. In April, 1985, the reciprocal cross to tetraploid *Tripsacum* was made using *Z. diploperennis* as pollen donor and *T. dactyloides* as pollen recipient, and U.S. Plant Pat. No. 7,977 for 'Tripsacorn', the hybrid from that cross, was issued Sep. 15, 1992. In January, 1988, *Z. diploperennis* was pollinated with pollen from a diploid (2n=36) *T. dactyloides.* U.S. Plant Pat. No. 9,640 for 'Sun Star', the hybrid from that cross, was issued Sep. 3, 1996.

On Jan. 26, 2002, *Z. diploperennis* was pollinated with pollen from *Tripsacum laxum.* The seed, planted May 27, 2002, germinated and grew into a normal, fully fertile plant named 'Venus Express' that is a perennial and produces viable fruits year-round in the greenhouse. The new plant has been propagated by rhizome divisions, cuttings, and anther culture. Various corn lines crossed with 'Venus Express' have produced fertile corn plants. This diploperennis-*Tripsacum* recombinant, like the recombinants 'Sun Dance', 'Tripsacorn', and 'Sun Star', provides a genetic bridge for moving genes from *Tripsacum* into corn using conventional plant breeding methods, and thereby establishing a link between these wild grasses and modern corn that may be beneficial in corn improvement breeding programs. Unique propagation of this plant through successive generations by means of rhizome divisions, cuttings, and anther culture have demonstrated that the new plant has not only retained the continuous and abundant production capability, but also that its distinguishing characteristics hold true from generation to generation and appear to be firmly fixed. Examination of the roots revealed that 'Venus Express' has well developed air passages referred to as aerenchyma. This property provides roots oxygen so they can tolerate flooded soils. It also allows the roots to grow deep below the hardpan, a characteristic that conveys good drought tolerance along with acid soil and aluminum tolerance, and gives the plant potential for use in bioremediation. Propagation has taken place in Durham, N.C. All activities including making the cross pollination between the two genera, growing the respective recombinant plant from a seed, and further reproducing the plant asexually from rhizomes, stem cuttings, and anther culture, took place in a greenhouse in Durham, N.C.

DESCRIPTION OF ILLUSTRATIONS

Figure 2:
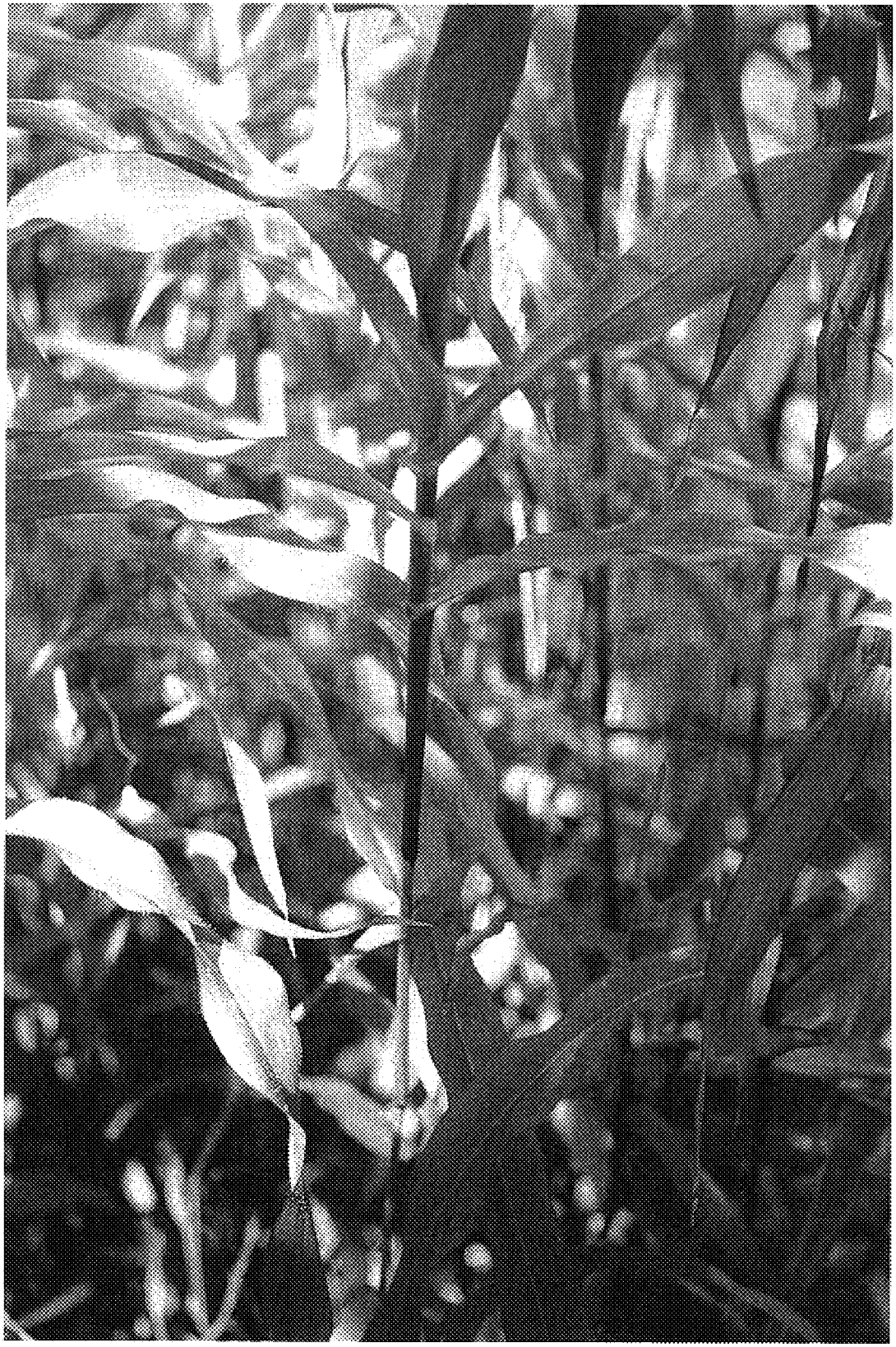
Figure 3:
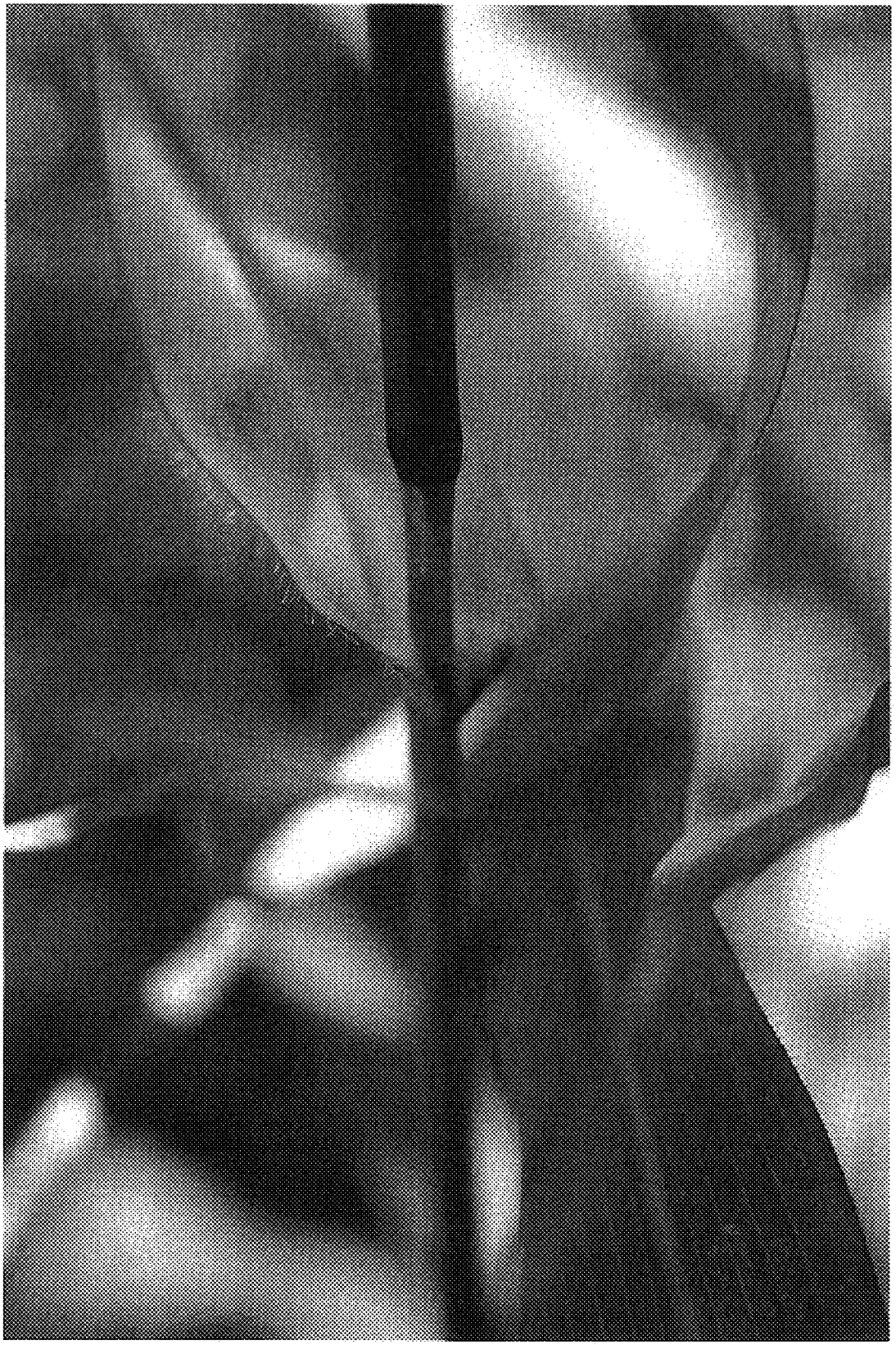
Figure 4:
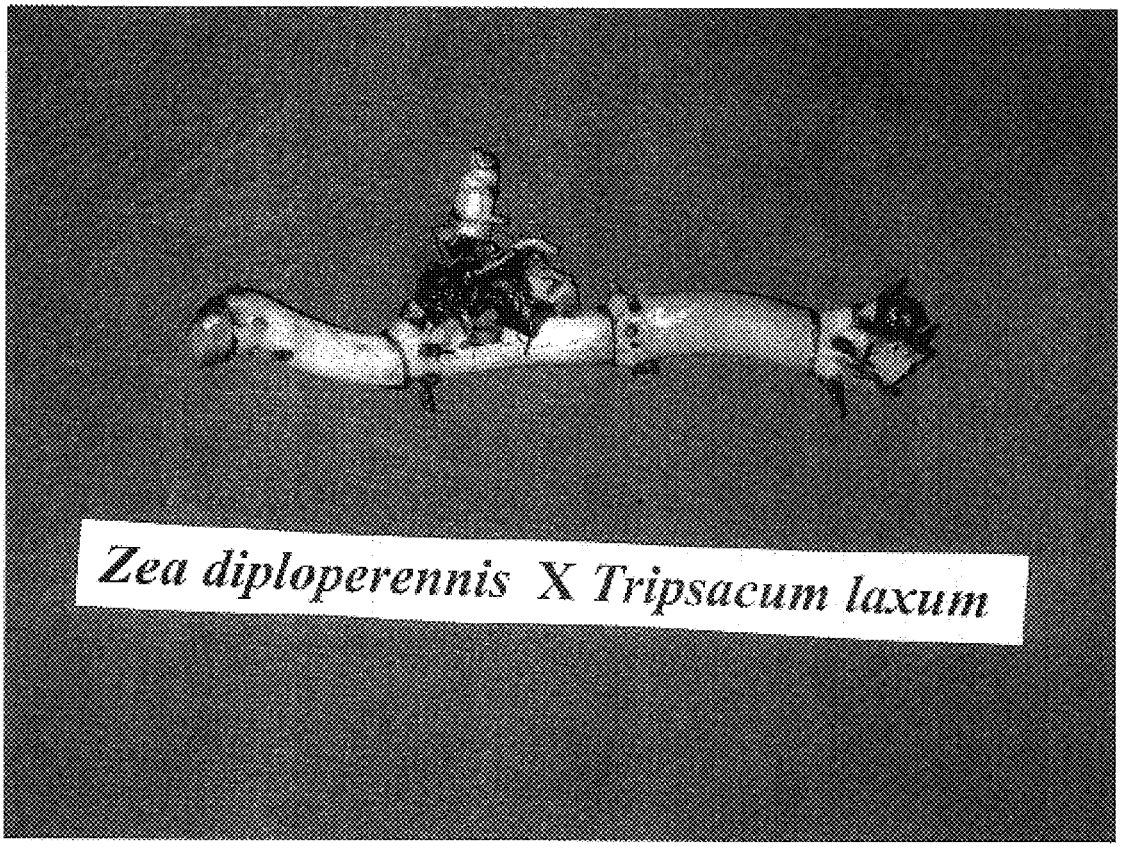
Figure 5:
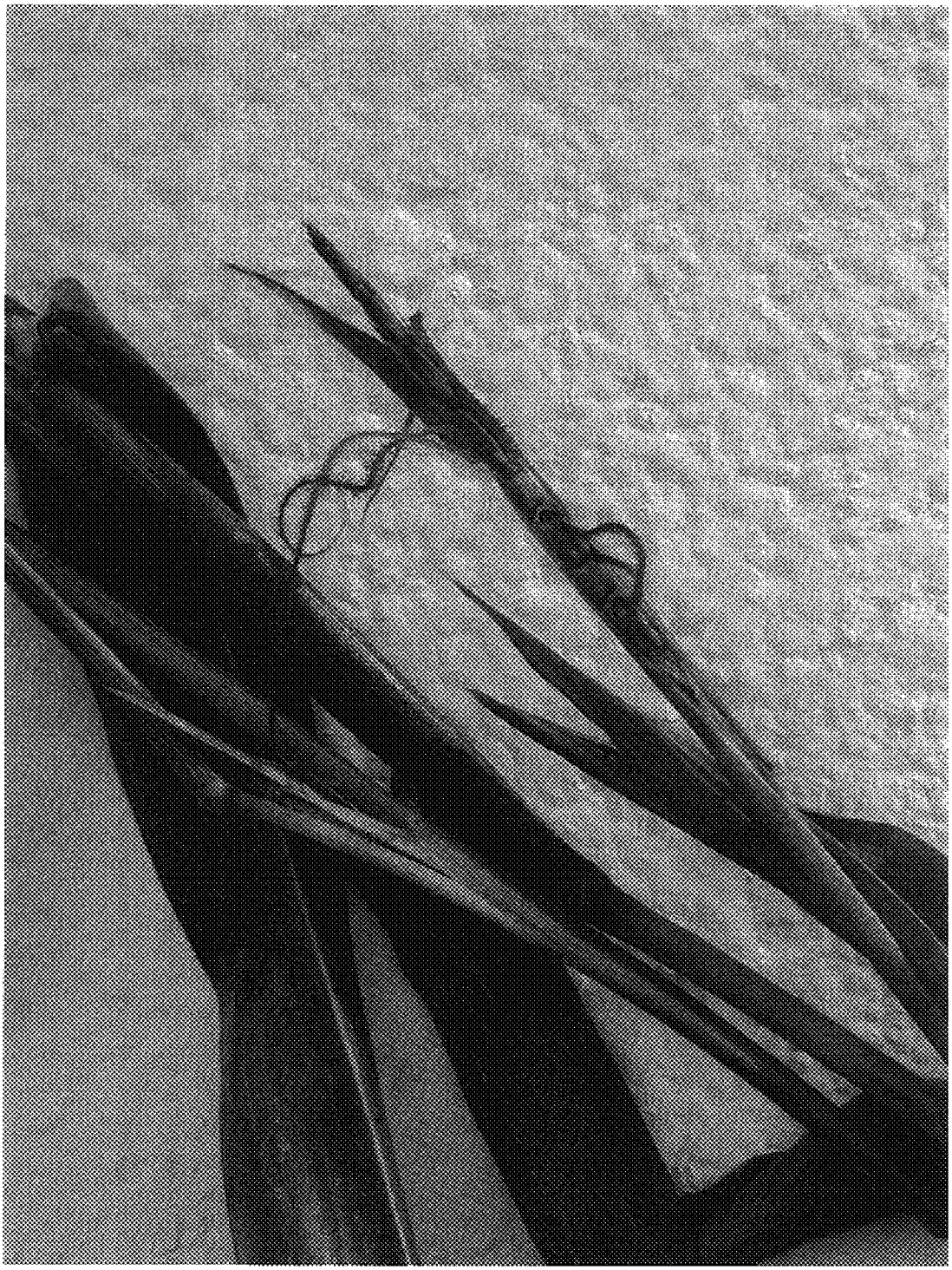

This new corn plant is illustrated by the accompanying full color photographs that include:

FIG. 1, a fully grown plant showing the characteristic habit of many culms growing from the base;

FIG. 2, a closeup of culms enwrapped by the red sheath;

FIG. 3, a closeup of the ciliate leaf margins;

FIG. 4, a rhizome;

FIG. 5, a distichously arranged pistillate spike with red styles, and

Figure 6:
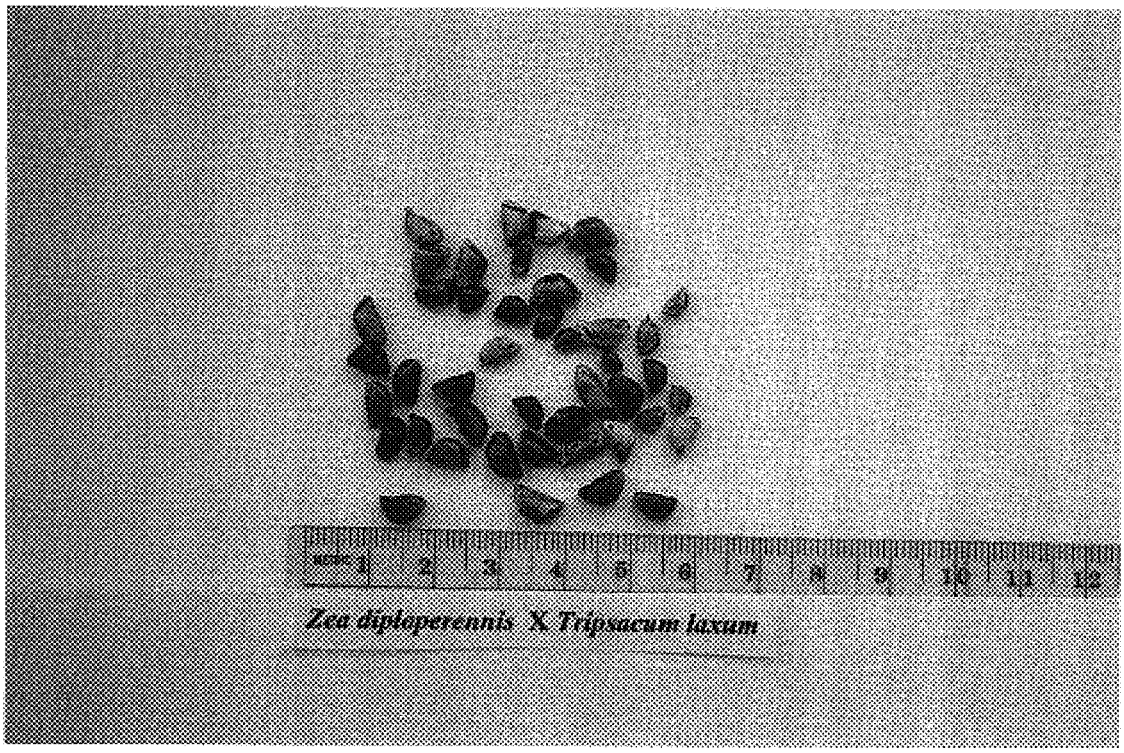
Figure 7:
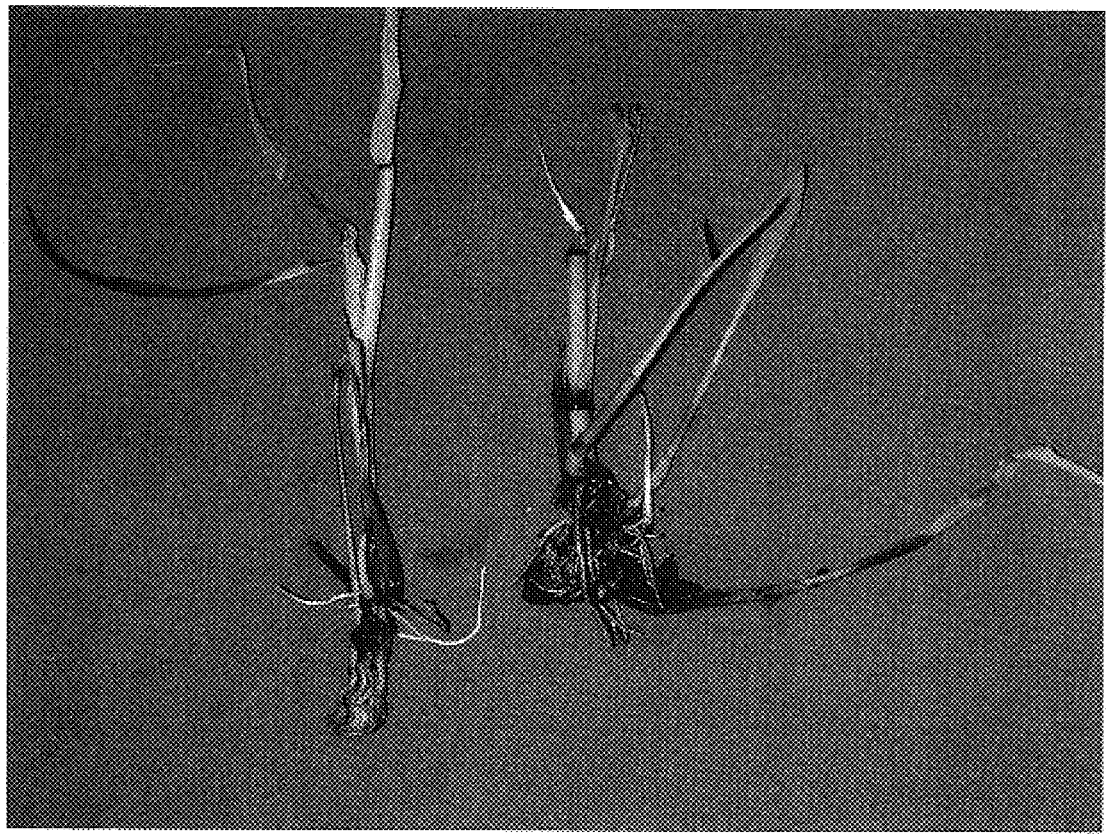
Figure 8:
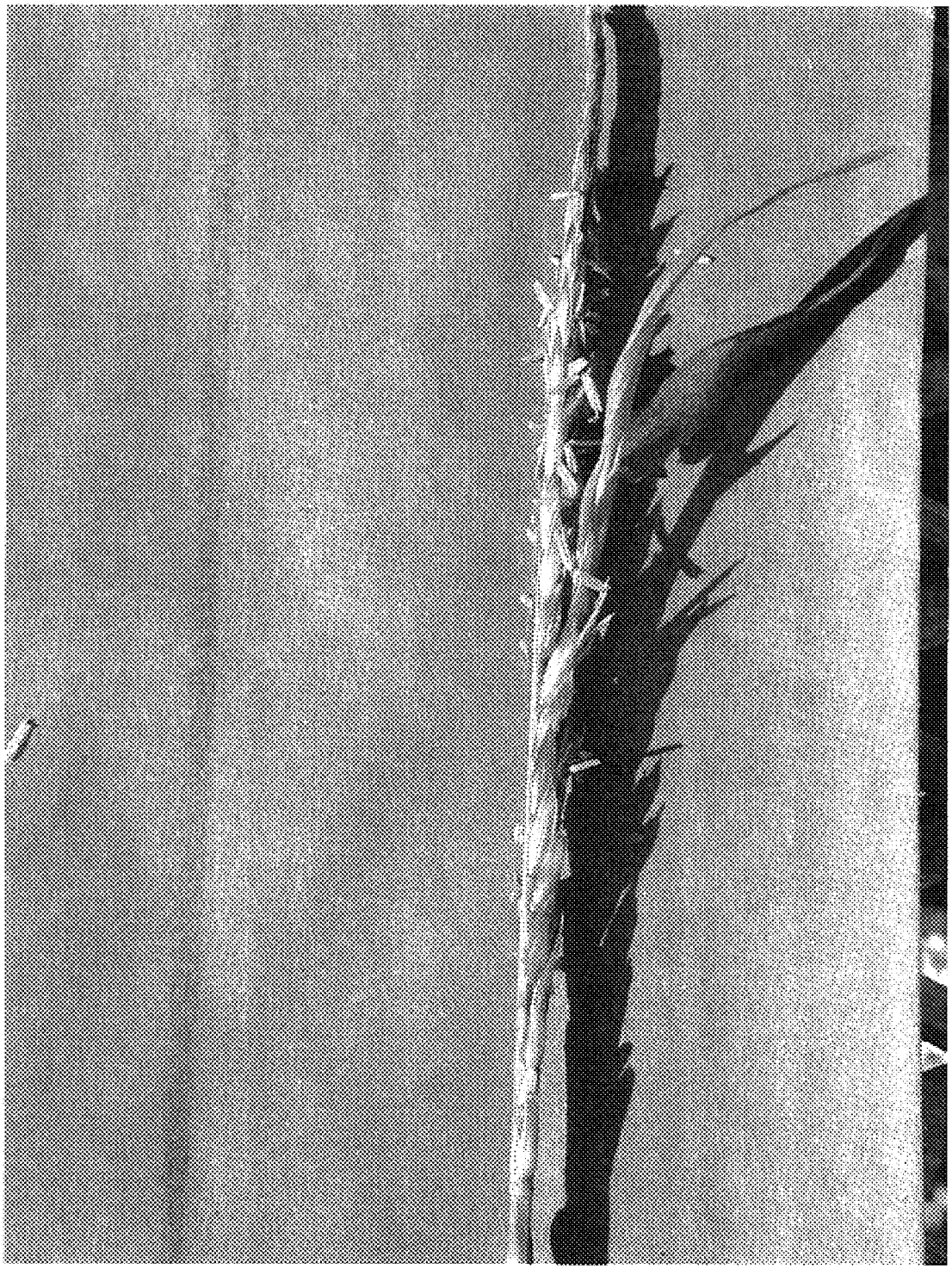

FIG. 6, mature seeds;

FIG. 7, rooted cuttings;

FIG. 8, a tassel branch showing a plantlet growing out of an anther, and

Figure 9:
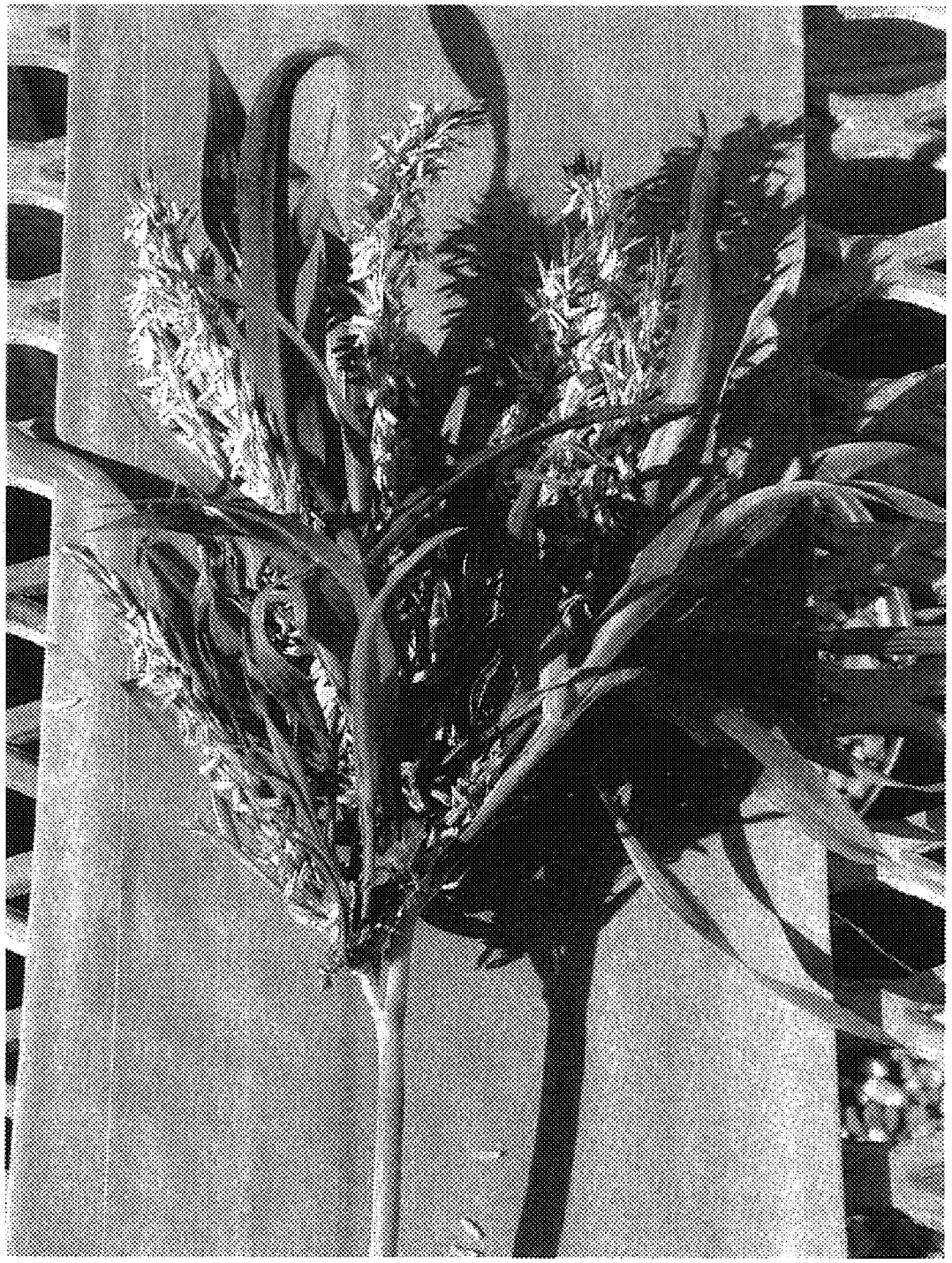

FIG. 9, a tassel with multiple plantlets growing out of anthers.

The plant:

Origin: Seedling.

Parentage:

*Seed parent.*—*Zea diploperennis* (2n=20). Provenance: Upper Las Joyas, Sierra de Manantlan, Jalisco, Mexico, Iltis, Nee & Guzman Acc. #1250, January 1979.

*Pollen parent.*—*Tripsacum laxum* (2n=72 Provenance: CEL 4873, Veracruz, Mexico, H. T. Stalker, November 1974.

Chromosome number: 2n=20.

Habit: Essentially erect; as many as 60 primary culms, usual number about 50.

Duration:

*Perennial.*—Sends out shoot from rhizomes.

Culm:

*Height.*—Up to 2.2 meters: slender, simple with occasional branching from the nodes of the culm; glabrous; round to slightly oval in cross section; Diameter 4.5 mm×7.5 mm. Color: light green (Pantone 14-0627 TP "Shadow Green").

*Nodes.*—Glabrous; internode length 8.5 cm.

*Sheath.*—Enwraps the culm, margins not united; margins ciliate; Color: deep red (Pantone #19-1726 TP "Cordovan") to light red (Pantone #18-1635 TP "State Rose").

*Ligule.*—Present on adaxial side of leaf at junction of blade and sheath; length: 3.6 mm; membranaceous, irregular edge, Color: light green (Pantone #14-0627 TP "Shadow Green").

Leaf blade: Alternate; distichous; sheathing base; parallel veined; narrowly linear, flat, thin.

*Length.*—26.0 cm. Width: 3.1 cm. Color: green (Pantone #18-0324 TP Calliste Green).

*Leaf tip.*—Attenuate.

*Entire margin.*—Ciliate, Color: red (Pantone #19-1629 TP "Ruby Wine").

*Midrib.*—Color: white (Pantone #11-0601 TP "Bright White").

*Adaxial surface.*—Hirsute.

*Abaxial surface.*—Glabrous.

*Prominent parallel veins.*—5 per 1.0 cm width.

Rhizome: Underground stem that produces buds at the nodes from which new plants emerge. Internode.—Round. Length: 2.5 cm. Diameter: 1.0 cm. Color: light beige (Pantone 13-1107TP "Whisper pink").

Inflorescence:

Blooming period: Continuous year-round in the greenhouse.

Monoecious: Separate male and female flowers on same plant.

Staminate flowers: May be of two types: one inflorescence type borne as paired spikes on a slender rachis forming a branched terminal spike, generally composed of two branches. Alternatively, staminate spikelets may be borne on a single spike at the summit of a culm or on the same spike and above the pistillate flowers.

*Axis.*—Stiff, continuous, ascending. Spikelet: Two-flowered, one sessile, one pedicellate; laterally compressed awnless; Length: 8.6 mm. Width: 3.2 mm. In pairs on one side of a persistent central axis.

*Pedicel length.*—3.9 mm.

*Glumes.*—Outer glume: cartilaginous, tapering to an acute tip, ciliate, flat, several nerved, margins scabrous. Inner glume: chartaceous.

Pollen viability: 84%.

Pistillate flowers: Borne in leaf axils; three or more pistillate spikelets per node, one sessile and others pedicellate; pedicel length: up to 27 cm; spikelets distichously arranged; pistillate flower consists of a single rowed spike of 4 to 7 trapezoidal caryopses in hard, shell-like fruitcases; may be enclosed in a single leaf sheath or not enclosed; caryopses disarticulate upon maturity.

*Styles.*—Pilose. Length: 8.75 cm.

*Color.*—Ranges from pastel parchment (Pantone #11-0603) to deep red when fully emerged (Pantone #19-1726 TP "Cordova").

*Length.*—9.0 cm.

Fruit: As many as 11 ears per culm per blooming period; flowers produced year-round.

Maturity: 45 days following fertilization.

Kernel (Dried): Angular caryopses in hard, shell-like fruitcases, disarticulate upon maturity:

Size: Length: 7.5 mm, Width: 4.5 mm, Thickness: 4.0 mm.

Shape: Trapezoidal.

Color: Ranges from dark brown (Pantone #181124 TP "Partridge") to light brown (Pantone #16-1320TP "Nougat") with dark brown speckles to beige (Pantone #13-1106TP "Pearl Gray") with brown speckles.

Weight: 20 seed (unsized samples): 1.5 gm.

Comparative parental characteristics:

Duration: *Zea diploperennis* perennial sends out shoots from underground bulbils. *Tripsacum laxum* perennial from rhizomes.

Culm: *Zea diploperennis* Culm round in cross section; Diameter: 2.5 cm; sheath tightly closed completely enwrapping the culm; Color: red (Pantone #19-1530 TP "Burnt Russet"), Internode length: 17.5 cm. *T. laxum* Culm oval in cross section; Diameter: 0.4 cm×1.5 cm; sheath splits apart and partially enwraps the culm, Color: red (Pantone #19-1726 TP "Cordova"), Internode length: 28.3 cm.

Leaf blade: *Z. diploperennis*. Length: 77.5 cm. Width 5.0 cm; margins pink serrulate from midsection of blade to tip; adaxial surface: hirsutullous; prominent veins: 6 per 1.0 cm width, Color: green (Pantone #18-0324 TP Calliste Green). *T. laxum*. Length: 75.0 cm. Width: 5.0 cm; margins scabrous; adaxial surface: glabrous; veins: 5 per 1.0 cm width.

Blooming period: *Z. diploperennis* twice a year, end of March and end of September for about a month. *T. laxum* from January to March.

Staminate flowers: *Z. diploperennis* borne in tassel with 6 to 7 branches at summit of culm. Total length staminate spike: 33.8 cm. Staminate spikelet pedicel length: 3 mm. Staminate spikelet outer glume length: 12.5 mm. *T. laxum* staminate flowers borne above pistillate flowers on a spike borne in a branching, pendulous terminal inflorescence with five to twenty branches; Total length staminate spike: 29.4 cm. Staminate spikelet pedicel length: 2.6 mm. Staminate spikelet outer glume length: 6.4 mm.

Pistillate flowers: *Z. diploperennis* caryopsis triangular in hard bony fruitcases; Length: 8 mm; Width: 4.5 mm; Color: black (Pantone #10-0303), dark brown (Pantone #10-1020) or brown speckled. *T. laxum* caryopsis in hard, rectangular fruitcases; Length: 7.0 mm; Width: 3.2 mm.

*Color.*—Brown (Pantone #18-1033TP "Dachshund").

*Style length.*—2.9 mm, Color: red (Pantone #19-1726 TP "Cordova").

Color reference: The Pantone Textile Color Guide. 1992. Pantone, Inc., Carlstadt, N.J. ISBN 1-881509-32-X.

COMPARISON TO 'SUN DANCE', 'TRIPSACORN' AND 'SUN STAR'

Although this plant is similar to 'Sun Dance', 'Tripsacorn', and 'Sun Dance', it is distinctive from these plants because it was derived from crossing *Z. diploperennis* with *T. laxum* (2n=72), section Fasciculata; whereas 'Sun Dance' and 'Tripsacorn' hybrids were derived from crossing *Z. diploperennis* with a tetraploid *T. dactyloides* (2n=72), section *Tripsacum*, and 'Sun Star' was derived from crossing *Z. diploperennis* with a diploid *T. dactyloides* (2n–36), section *Tripsacum*. In contrast to the sessile pair of staminate flowers characteristic of *T. dactyloides* and section *Tripsacum* in general, *T. laxum* has one sessile and one pedicillate staminate member of the pair of staminate flowers, which is characteristics of the *Tripsacum* members of section Fasciculata. Venus Express is distinguished from the three *diploperennis-T. dactyloides* recombinants by its smaller leaves, more numerous culms, and year-round flowering. *T. laxum* and *diploperennis* are used as forage plants. The greater number of culms and year-round flowering of Venus Express are traits not characteristic of either parent that give it added value as a forage crop in addition to its capacity to serve as a genetic bridge to move *T. laxum* genes into corn.

I claim:

1. A new and distinct variety of corn plant, substantially as herein shown and described, that is characterized by its profuse production of fruit, perennial habit, vigorous vegetative production of culms, roots with aerenchyma, asexual reproduction by rhizomes, stem cuttings, and anther culture, and its good combining ability with corn that permits movement of new genes and agronomic traits into corn using conventional plant breeding methods.

* * * * *